United States Patent [19]

Quentin-Millet

[11] Patent Number: 5,618,541
[45] Date of Patent: Apr. 8, 1997

[54] **VACCINE AGAINST *NEISSERIA MENINGITIDIS* INFECTIONS**

[75] Inventor: Marie-José Quentin-Millet, Villeurbanne, France

[73] Assignee: Pasteau Merieux Serums et Vaccins, Lyon, France

[21] Appl. No.: 66,167

[22] PCT Filed: Sep. 29, 1992

[86] PCT No.: PCT/FR92/00905

§ 371 Date: Jun. 2, 1993

§ 102(e) Date: Jun. 2, 1993

[87] PCT Pub. No.: WO93/06861

PCT Pub. Date: Apr. 15, 1993

[30] Foreign Application Priority Data

Oct. 3, 1991 [FR] France ................................ 91 12177

[51] Int. Cl.$^6$ ............................................... A61K 31/075
[52] U.S. Cl. ........................... 424/250.1; 424/249.1; 435/871
[58] Field of Search ......................... 424/92, 249.1, 424/250.1, 192; 435/871; 530/400

[56] References Cited

FOREIGN PATENT DOCUMENTS

87/02678  5/1987  WIPO.
90/12591  1/1990  WIPO.

OTHER PUBLICATIONS

N. Banerjee-Bhatnagar and Carle E. Frasch, "Expression of *Neisseria meningitidis* Iron-Regulated Outer Membrane Proteins, Including 1 70-Kilodalton Transferrin Receptor, and Their Potential for Use as Vaccines," *Infection and Immunity*, vol. 58, No. 9, Sep. 1990, pp. 2875–2881.

Anthony B. Schryvers and Leigh J. Morris, "Identification and Characterization of the Human Lactoferrin–Binding Protein from *Neisseria meningitidis*," *Infection and Immunity*, vol. 56, May 1988, pp. 1144–1149.

Griffiths et al; FEMS Microbiology Letters 69:31–36, 1990.
Saukkonen et al; Vaccine 7:325–328, 1989.
Schryvers et al; Can. J. Microbiol 35:409–415, 1989.
Mackinnen et al, Microbiol Pathogenesis 12:415–420, 1992.
Sacchi et al Vaccine 13(1):112–118, 1995.
Zollinger et al, Trans. Royal Soc. Trop. Med Hyg. 85 Suppl. 1 37–43, 1991.
Zollinger et al, Infect. Immun. 40(1):257–264, 1983.

*Primary Examiner*—James C. Housel
*Assistant Examiner*—Julie Krsek-Staples
*Attorney, Agent, or Firm*—Burns, Doane, Swecker & Mathis, L.L.P.

[57] ABSTRACT

A vaccinal pharmaceutical composition which comprises, as therapeutic agents, at least a first and a second molecule capable of binding to human transferrin; the said first molecule originating from a first strain of *N. meningitidis* which possesses a human transferrin receptor in which the lower molecular weight subunit (Tbp2) is recognised by an antiserum to the receptor of *N. meningitidis* strain 2394 (receptor 2394) and is not recognised by an antiserum to the receptor of *N. meningitidis* strain 2169 (receptor 2169); and at least a second molecule originating from a second strain of *N. meningitidis* which possesses a human transferrin receptor in which the lower molecular weight subunit (Tbp2) is recognised by an anti-receptor 2169 antiserum and is not recognised by an anti-receptor 2394 antiserum.

**9 Claims, 1

VACCINE AGAINST *NEISSERIA MENINGITIDIS* INFECTIONS

The present invention relates to a vaccinal pharmaceutical composition intended for the prevention of meningitis caused by *Neisseria meningitidis*.

Generally speaking, meningitis is either of viral origin or of bacterial origin. The bacteria mainly responsible are *N. meningitidis* and *Haemophilus influenzae*, which are implicated, respectively, in approximately 40 and 50% of cases of bacterial meningitis.

*N. meningitidis* accounts for approximately 600 to 800 cases of meningitis per annum in France. In the USA, the number of cases amounts to approximately 2,500 to 3,000 per annum.

The species *N. meningitidis* is subdivided into serogroups according to the nature of the capsular polysaccharides. Although a dozen serogroups exist, 90% of cases of meningitis are attributable to 3 serogroups: A, B and C.

There are effective vaccines based on capsular polysaccharides to prevent meningitis caused by *N. meningitidis* serogroups A and C. These polysaccharides, as such, exhibit little or no immunogenicity in infants under 2 years of age, and do not induce immune memory. However, these drawbacks may be overcome by conjugating these polysaccharides to a carrier protein.

On the other hand, the polysaccharide of *N. meningitidis* group B exhibits little or no immunogenicity in man, either in conjugated or in unconjugated form. Thus, it is seen to be highly desirable to seek a vaccine against meningitis induced by *N. meningitidis*, in particular of serogroup B, other than a vaccine based on polysaccharide.

To this end, various proteins of the outer membrane of *N. meningitidis* have already been proposed. Special attention has focused on the membrane receptor for human transferrin.

Generally speaking, the large majority of bacteria require iron for their growth, and have developed specific systems for acquiring this metal. As regards *N. meningitidis* in particular, which is a strict pathogen of man, the iron can be abstracted only from human iron-transport proteins such as transferrin and lactoferrin, since the amount of iron in free form is negligible in man (of the order of $10^{-18}M$), and in any case insufficient to permit bacterial growth.

Thus, *N. meningitidis* possesses a human transferrin receptor and a human lactoferrin receptor, which enable it to bind these iron-chelating proteins and thereafter to take up the iron needed for its growth.

The transferrin receptor of *N. meningitidis* strain B16B6 has been purified by Schryvers et al. (WO 90/12591) from a membrane extract. This protein as purified evidently consists essentially of two types of polypeptide: a polypeptide of high apparent molecular weight of 100 kD and a polypeptide of lower apparent molecular weight of approximately 70 kD, as visualised after polyacrylamide gel electrophoresis in the presence of SDS.

The product of the purification carried out, in particular, by Schryvers is referred to, by arbitrary definition and for the requirements of the present patent application, as the transferrin receptor, and the polypeptides of which it consists are referred to as subunits. In the text below, the subunits of high molecular weight and of lower molecular weight are referred to as Tbp1 and Tbp2, respectively.

Figure 1:
FIG. 1 is an SDS-PAGE gel with 7.5% acrylamide, in which columns A and B correspond to the receptors of *N. meningitidis* strains 2169 and 2394, respectively. The arrows pointing horizontally indicate the position of the reference proteins of known apparent molecular mass (94 kD, phosphorylase B; 67 kD, albumin).

It has now been found that there are at least two types of strain which differ in the constitution of their respective transferrin receptors. This was demonstrated by studying membrane extracts of several tens of strains of *N. meningitidis* of miscellaneous origins. These membrane extracts were first subjected to SDS-PAGE gel electrophoresis and then electrotransferred onto nitrocellulose sheets. These nitrocellulose sheets were incubated:

a) in the presence of a rabbit antiserum directed towards the transferrin receptor purified from *N. meningitidis* strain B16B6, also referred to as 2394;

b) in the presence of a rabbit antiserum directed towards the transferrin receptor purified from *N. meningitidis* strain 2169; or c) in the presence of human transferrin conjugated to peroxidase.

As regards a) and b), the recognition of the subunits of the transferrin receptor is visualised by adding an anti-rabbit immunoglobulins antibody coupled to peroxidase, followed by addition of the substrate for this enzyme.

Tables I and II hereinbelow show the profile of some representative strains as seen on SDS-PAGE gel containing 7.5% polyacrylamide; the bands are characterised by their apparent molecular weight expressed in kilodaltons (kD):

TABLE I

| | Strains | | |
|---|---|---|---|
| | 2394 (B; 2a; P1.2:L2.3) 2228 (B; nd) 2170 (B; 2a:P1.2:2:L3) | 2234 (Y; nd) 2154 (C; nd) 2248 (B; nd) | 550 (C; 2a:) 179 (C; 2a:P1.2) |
| Detection with anti-receptor 2394 antiserum | 93 68 | 93 69 | 99 69 |
| Detection with anti-receptor 2169 antiserum | 93 | 93 | 99 |
| Detection with transferrin-peroxidase | 68 | 69 | 69 |

NB: The symbols in brackets denote, in order, the serogroup, serotype, subtype and immunotype.

TABLE II

| | Strains | | | | | | | | |
|---|---|---|---|---|---|---|---|---|---|
| | 2169 (B:9: P1.9) | 1000 (B:nd) | 1604 (B:nd) | 132 (C:15: P1.16) | 1001 (A:4: P1.9) | 876 (B:19: P1.6) | 1951 (A:nd) | 2449 (B:nd) | 867 (B:2b: P1.2) |
| Detection with anti-receptor 2394 antiserum | 96 | 98 | 98 | 98 | 98 | 96 | 94 | 94 | 93 |
| Detection with anti-receptor | 96 | 98 | 98 | 98 | 98 | 96 | 94 | 94 | 93 |

TABLE II-continued

| | Strains | | | | | | | | |
|---|---|---|---|---|---|---|---|---|---|
| | 2169 (B:9: P1.9) | 1000 (B:nd) | 1604 (B:nd) | 132 (C:15: P1.16) | 1001 (A:4: P1.9) | 876 (B:19: P1.6) | 1951 (A:nd) | 2449 (B:nd) | 867 (B:2b: P1.2) |
| 2169 antiserum | 87 | 85 | 83 | 81 | 79 | 88 | 87 | 85 | 85 |
| Detection with transferrin-peroxidase | 87 | 85 | 83 | 81 | 79 | 88 | 87 | 85 | 85 |

NB: The symbols in brackets denote, in order, the serogroup, serotype, subtype and immunotype.

The results appearing in the first 2 lines of the tables show that there are two types of strains:

The first type (Table I) corresponds to strains which possess a receptor in which both of the subunits are recognised by anti-receptor 2394 antiserum while only the high molecular weight subunit is recognised by anti-receptor 2169 antiserum.

The second type (Table II) corresponds to strains which possess a receptor in which both of the subunits are recognised by anti-receptor 2169 antiserum while only the high molecular weight subunit is recognised by anti-receptor 2394 antiserum.

Consequently, there exists an antigenic diversity in respect of the lower molecular weight subunit. This diversity is, however, limited since it resolves into 2 major types, in contrast to the suggestion made by Griffiths et al., FEMS Microbiol. Lett. (1990) 69: 31.

[Moreover, it will be noted that, irrespective of the type of strain, the subunit capable of binding to transferrin is always the lower molecular weight subunit (Tables I and II, third line of results).]

In accordance with these findings, it had been tempting to conclude that an effective vaccine against all *N. meningitidis* infections could be adequately composed of a transferrin receptor or exclusively of its high molecular weight subunit, irrespective of the strain of origin of the receptor, since this subunit is recognised by both types of antiserum.

Surprisingly, this has now been found not to be the case, inasmuch as the high molecular weight subunit does not appear to be capable of inducing the production of neutralising type antibodies. Only the smaller of the 2 subunits of the receptor appears to be capable of fulfilling this function. Since this lower molecular weight subunit is characterised by a significant antigenic variation from the first type to the second type of strain, a single type of transferrin receptor should not be sufficient for vaccinating against all *N. meningitidis* infections.

Thus, the invention provides for:

i) A vaccinal pharmaceutical composition which comprises, as therapeutic agents, at least a first and a second molecule capable of binding to human transferrin; the said first molecule originating from a first strain of *N. meningitidis* which possesses a human transferrin receptor at least consisting of a high molecular weight subunit (Tbp1) and a lower molecular weight subunit (Tbp2), and in which the lower molecular weight subunit (Tbp2) is recognised by an antiserum to the receptor of *N. meningitidis* strain 2394 (receptor 2394) and is not recognised by an antiserum to the receptor of *N. meningitidis* strain 2169 (receptor 2169); and the said second molecule originating from a second strain of *N. meningitidis* which possesses a human transferrin receptor at least consisting of a high molecular weight subunit (Tbp1) and a lower molecular weight subunit (Tbp2), and in which the lower molecular weight subunit (Tbp2) is recognised by an anti-receptor 2169 antiserum and is not recognised by an anti-receptor 2394 antiserum;

ii) A vaccination kit containing:

a) A pharmaceutical composition which comprises, as therapeutic agent, at least a first molecule capable of binding to human transferrin; the said first molecule originating from a first strain of *N. meningitidis* which possesses a human transferrin receptor at least consisting of a high molecular weight subunit and a lower molecular weight subunit, and in which the lower molecular weight subunit is recognised by an antiserum to the receptor of *N. meningitidis* strain 2394 (receptor 2394) and is not recognised by an antiserum to the receptor of *N. meningisidis* strain 2169 (receptor 2169);

b) A pharmaceutical composition which comprises, as therapeutic agent, at least a second molecule capable of binding to human transferrin; the said second molecule originating from a second strain of *N. meningitidis* which possesses a human transferrin receptor at least consisting of a high molecular weight subunit and a lower molecular weight subunit, and in which the lower molecular weight subunit is recognised by an anti-receptor 2169 antiserum and is not recognised by an anti-receptor 2394 antiserum; and c) Instructions for the concomitant or consecutive administration of the compositions a) and b);

iii) The combined therapeutic use of at least a first and a second molecule capable of binding to human transferrin; the said first molecule originating from a first strain of *N. meningitidis* which possesses a human transferrin receptor at least consisting of a high molecular weight subunit and a lower molecular weight subunit, and in which the lower molecular weight subunit is recognised by an antiserum to the receptor of *N. meningitidis* strain 2394 (receptor 2394) and is not recognised by an antiserum to the receptor of *N. meningisidis* strain 2169 (receptor 2169); and the said second molecule originating from a second strain of *N. meningitidis* which possesses a human transferrin receptor at least consisting of a high molecular weight subunit and a lower molecular weight subunit, and in which the lower molecular weight subunit is recognised by an anti-receptor 2169 antiserum and is not recognised by an anti-receptor 2394 antiserum; and iv) A method of vaccination against *N. meningitidis* infections, which comprises the act of administering an effective amount, from a therapeutic standpoint, of at least a first and a second molecule capable of binding to human transferrin, concomitantly or consecutively, to a subject requiring such a vaccinal treatment; the said first molecule originating from a first strain of *N.*

*meningitidis* which possesses a human transferrin receptor at least consisting of a high molecular weight subunit and a lower molecular weight subunit, and in which the lower molecular weight subunit is recognised by an antiserum to the receptor of *N. meningitidis* strain 2394 (receptor 2394) and is not recognised by an antiserum to the receptor of *N. meningitidis* strain 2169 (receptor 2169); and the said second molecule originating from a second strain of *N. meningitidis* which possesses a human transferrin receptor at least consisting of a high molecular weight subunit and a lower molecular weight subunit, and in which the lower molecular weight subunit is recognised by an anti-receptor 2169 antiserum and is not recognised by an anti-receptor 2394 antiserum.

"Molecule capable of binding to human transferrin" is understood to mean either a human transferrin receptor originating from *N. meningitidis* (that is to say a molecule comprising, in particular, 2 types of subunit), or exclusively the subunit of the receptor, capable of binding to human transferrin, as well as a fragment or an analogue of this subunit.

A transferrin receptor may be obtained in purified form from a strain of *N. meningitidis* previously cultured in a medium deficient in iron in free form, in particular according to the method of Schryvers et al., WO 90/12591, described in a similar manner in Schryvers et al., Infect. Immun. (1988) 56 (5):1144. Alternatively, a transferrin receptor originating from a strain of *N. meningitidis* may be produced by employing genetic engineering techniques. The DNA fragment or fragments coding for the subunits of the receptor may be expressed jointly or separately in a heterologous expression system (e.g. bacterium, yeast, mammalian cell). The subunits, in free form or associated in the form of the receptor, are, in this case, collected from a culture and purified. When the subunits are produced in this way in free form, provision may be made for reassociating them in the form of the receptor by subjecting them to a suitable treatment.

The subunit capable of binding to human transferrin (lower molecular weight subunit) may be obtained in purified form (that is to say dissociated and isolated from the high molecular weight subunit), in particular, from a receptor purified according to the method of Schryvers et al., by subjecting the receptor to the action of a strongly denaturing agent such as 8M urea or 6M guanidine HCl, and then separating the dissociated subunits by standard chromatographic methods such as ion exchange chromatography or gel filtration. Alternatively, the subunit may be produced according to genetic engineering methods. These methods are, in addition, entirely suited to the production of fragments or analogues of the subunit.

As an example, the subunits Tbp1 and Tbp2 of the strains 2394 and 2169 are described by reference to their amino acid sequences as shown in the sequence identifiers Nos. 1 to 4 (SEQ ID No. 1 to 4).

"Fragment of the subunit capable of binding to human transferrin" is understood to mean a peptide having an amino acid sequence which is included in the sequence of the subunit. "Analogue of the subunit capable of binding to human transferrin" is understood to mean a protein having an amino acid sequence which exhibits an at least 80%, preferably at least 90% and, as an absolute preference, at least 95% homology with the sequence of the subunit. For the purposes of the present invention, it should be clearly understood that such a fragment or such an analogue must retain the immunogenic properties of the subunit.

*N. meningitidis* strains 2394 (B:2a:P1.2:L2.3) and 2169 (B:9:P1.9:L3.7), which are commonly used in laboratories, are available to the public from the Collection of the Pasteur Institute, 25 rue du Dr Roux 75015 Paris, under the respective registration numbers CIP 7908 and CIP 7917.

Furthermore, the anti-receptor antisera which are required in order to distinguish the strains of *N. meningitidis* may be obtained as follows:

A receptor is first purified from an initial strain (2394 or 2169) according to the method of Schryvers et al. Albino New Zealand rabbits receive subcutaneously and intramuscularly 100 μg of the receptor in the presence of Freund's complete adjuvant. 21 days and 42 days after the first injection, the rabbits again receive 100 μg of the purified receptor, but on these occasions in the presence of Freund's incomplete adjuvant. 15 days after the last injection, the animals' serum is withdrawn, then decomplemented and filtered through a membrane of porosity 0.45 μm. The filtrate is thereafter exhaustively extracted by contact with the initial strain which, to this end, has been cultured beforehand in the presence of iron (under these conditions, synthesis of the transferrin receptor is repressed). The contacting procedure is as follows: 10 ml of the filtrate are added to $10^{10}$ cfu (colony forming units) of a culture of the initial strain. Adsorption is carried out overnight at 4° C. with agitation. The bacteria are then removed by centrifugation. The supernatant is recovered and then subjected again to 2 successive adsorption operations as described above.

The type of a strain (with respect to the nature of its transferrin receptor) may be identified from membrane extracts derived from cultures deficient in iron in free form, employing conventional techniques such as SDS-PAGE gel electrophoresis, followed by immunoblotting using an antiserum such as that described above.

The first molecule participating in the vaccinal composition originates from a first strain of *N. meningitidis* which possesses a transferrin receptor essentially consisting of (i) a subunit of high molecular weight, advantageously of 100 to 90 kD and preferably of 93–95 kD approximately, and (ii) a subunit of lower molecular weight, advantageously of 75 to 60 kD and preferably of 72 to 65 kD, and, as an absolute preference, respectively (i) of 93 kD and (ii) of 67–70 kD approximately.

The second molecule participating in the vaccinal composition originates from a second strain of *N. meningitidis* which possesses a transferrin receptor essentially consisting of (i) a subunit of high molecular weight, advantageously of 100 to 90 kD, preferably of 100 to 95 kD and, as an absolute preference, of 98 kD approximately, and (ii) a subunit of lower molecular weight, advantageously of 90 to 80 kD, preferably of 87 to 85 kD and, as an absolute preference, of 87 kD approximately.

The molecular weights stated above are apparent molecular weights as visualised after electrophoresis of a receptor purified on SDS-PAGE gel. Such an electrophoresis may be carried out according to the method of Laemmli illustrated as follows:

A polyacrylamide gel (16 cm×20 cm×1 mm in thickness) comprising a 5% pregel and a 7.5% separating gel is first prepared in electrophoresis buffer (Tris 6 g/l, glycine 28.8 g/l, 0.1% SDS).

In addition, 50 μl of sample buffer (62 mM Tris-HCl pH 6.8, 2% SDS, 5% β-mercaptoethanol, 1% glycerol, 0.001% bromophenol blue) are added to 50 μl of a solution of purified receptor at a concentration of 0.6 mg/ml (in 50 mM phosphate buffer pH 8.0 containing 0.05% Sarkosyl). The mixture is incubated for 5 min in a boiling water bath. 17 μl (equivalent to 5 µg of protein) of the sample thus prepared are placed in a well in the gel. A sample prepared in a similar manner containing molecular weight markers is added in parallel. Electrophoresis is carried out in electrophoresis buffer at 50 volts for 15 hours. The gel is fixed and stained with Coomassie blue.

Generally speaking, the first or the second molecule which is useful for the purposes of the present invention can originate from a strain of *N. meningitidis* of any serogroup. Advantageously, the first or the second molecule originates from a strain of *N. meningitidis* serogroup B. Preferably, the first and second molecules originate respectively from a first and a second strain of *N. meningitidis* serogroup B.

According to an absolutely preferred aspect of the invention, the first molecule originates from the strain 2394 while the second molecule originates from the strain 2169.

A pharmaceutical composition according to the invention may be manufactured in a conventional manner. In particular, the therapeutic agent or agents according to the invention is/are combined with a diluent or vehicle which is acceptable from a pharmaceutical standpoint. A composition according to the invention may be administered by any conventional route in use in the vaccine field, especially subcutaneously, intramuscularly or intravenously, for example in the form of an injectable suspension. The administration can take place in a single dose or in a dose repeated one or several times after a certain time interval. The appropriate dosage varies in accordance with various parameters, for example with the individual being treated or with the mode of administration.

The invention is described in greater detail in the examples below and with reference to FIG. 1, which illustrates an electrophoresis on SDS-PAGE gel with 7.5% polyacrylamide, in which the columns A and B correspond to the receptors of *N. meningitidis* strains 2169 and 2394, respectively. The arrows pointing horizontally indicate the position of the reference proteins of known apparent molecular mass (94 kD, phosphorylase B; 67 kD, albumin).

EXAMPLE 1

Purification of the Transferrin Receptor from the Strain 2394

1A—Culture

A lyophilisate of *N. meningitidis* strain 2394 is taken up in approximately 1 ml of Mueller-Hinton broth (MHB, Difco). The bacterial suspension is then plated out on Muller-Hinton solid medium containing cooked blood (5%).

After 24 h of incubation at 37° C. in an atmosphere containing 10% of $CO_2$, the bacterial lawn is collected in order to inoculate 150 ml of MHB pH 7.2, distributed in three 250-ml Erlenmeyers. Incubation is carried out for 3 h at 37° C. with agitation. Each of the 3 cultures so produced permits the inoculation of 400 ml of MHB pH 7.2 supplemented with 30 μM of ethylenediaminedi(o-hydroxyphenylacetic acid) (EDDA, Sigma), which is a chelating agent for iron in free form.

After 16 h of culture at 37° C. with agitation, the cultures are monitored for their purity by microscopic observation after Gram staining. The suspension is centrifuged and the pellet containing the microbes is weighed and stored at −20° C.

1B—Purification

The purification method is essentially that described by Schryvers et al. (supra).

The bacterial pellet obtained in 1A is thawed and then resuspended in 200 ml of 50 mM Tris-HCl buffer, pH 8.0 (buffer A). The suspension is centrifuged for 20 min at 15,000 x g at 4° C. The pellet is recovered and then resuspended in buffer A at a final concentration of 150 g/l. 150-ml fractions are treated for 8 min at 800 bars in a cell lyser working under high pressure (Rannie, model 8.30H). The cell lysate thereby obtained is centrifuged for 15 min at 4° C. at 15,000 x g. The supernatant is recovered and then centrifuged for 75 min at 4° C. at 200,000 x g.

After removal of the supernatant, the pellet is taken up in buffer A and, after protein assay by the Lowry method, the concentration of the suspension is adjusted to 5 mg/ml.

1.75 mg of biotinylated human transferrin are then added to 1.4 ml of the membrane suspension according to the method described by Schryvers. The final concentration of the membrane fraction is 4 mg/ml. The mixture is incubated for 1 hour at 37° C. and then centrifuged at 100,000 x g for 75 minutes at 4° C. The membrane pellet is taken up with buffer A containing 0.1M NaCl, and incubated for 60 min at room temperature.

After solubilisation, a certain volume of 30% (w/v) N-LauroylSarkosine and of 500 mM EDTA are added to this suspension so that the final concentrations of Sarkosyl and EDTA are 0.5% and 5 mM, respectively. After incubation for 15 min at 37° C. with agitation, 1 ml of streptavidin-agarose resin (Pierce), previously washed in buffer A, is added. The suspension is incubated for 15 min at room temperature and then centrifuged at 1,000 x g for 10 min. The resin is then packed in a column and the direct eluate is discarded.

The resin is washed with 3 column volumes of 50 mM Tris-HCl buffer pH 8.0 containing 1M NaCl, 10 mM EDTA, 0.5% Sarkosyl (buffer B), and then with one column volume of buffer B containing 750 mM guanidine HCl. The transferrin receptor is then eluted with buffer B containing 2M guanidine HCl, 0.05% Sarkosyl. The eluate is collected in fractions whose volume corresponds to 1 Vol. in Lubes containing 1 Vol. of 50 mM Tris-HCl pH 8.0, 1M NaCl. The optical density of the eluate at 280 nm is measured at the column outlet using a UV detector.

The fractions corresponding to the elution peak are collected, dialysed against 10 mM phosphate buffer, pH 8.0 containing 0.05% Sarkosyl and lyophilised. The lyophilisate is taken up in water at a 10-fold higher concentration. The solution is dialysed a second time against 50 mM phosphate buffer pH 8.0 containing 0.05% Sarkosyl (buffer C), and the solution is then filtered through a membrane of porosity 0.22 μm.

The protein content is determined and adjusted to 1 mg/ml by adding buffer C, under aseptic conditions. This preparation is stored at −70° C.

EXAMPLE 2

Purification of the Transferrin Receptor from the Strain 2169

Culturing of the strain 2169 and purification of the transferrin receptor are performed under conditions identical to those described in Example 1.

EXAMPLE 3

Vaccinal Pharmaceutical Composition Intended for Preventing *N. meningitidis* Infections The sterile solutions obtained in Examples 1 and 2 are thawed. In order to prepare one liter of vaccine containing 100 µg/ml of each of the active principles, the following solutions are mixed under sterile conditions:

| | |
|---|---|
| Solution of receptor 2394 at a concentration of 1 mg/ml in buffer C | 100 ml |
| Solution of receptor 2169 at a concentration of 1 mg/ml in buffer C | 100 ml |
| Buffered physiological saline (PBS), pH 6.0 | 300 ml |
| Aluminium hydroxide containing 10 mg $Al^{+++}$/ml | 50 ml |
| Merthiolate, 1% (w/v) in PBS | 10 ml |
| PBS qs | 1,000 ml |

EXAMPLE 4

Demonstration of the Importance of the Lower Molecular Weight Subunit as a Vaccinal Agent Albino New Zealand rabbits receive subcutaneously and intramuscularly 100 µg of the receptor 2394 or 2169 (as obtained in Example 1 or 2), in the presence of Freund's complete adjuvant. 21 and 42 days after the first injection, the rabbits again receive 100 µg of the purified receptor, but this time in the presence of Freund's incomplete adjuvant. 15 days after the last injection, the animals' serum is withdrawn, then decomplemented and filtered through a membrane of porosity of 0.45 µm. The filtrate is thereafter exhaustively extracted by contact with the initial strain (2394 or 2169) which, to this end, has been cultured beforehand in the presence of iron in free form (under these conditions, synthesis of the transferrin receptor is repressed). The contacting procedure is as follows: 10 ml of the filtrate are added to $10^{10}$ cfu (colony forming units) of a culture of the initial strain. Adsorption is carried out overnight at 4° C. with agitation. The bacteria are then removed by centrifugation. The supernatant is recovered and then subjected again to 2 successive adsorption operations as described above.

A dilution series of each of the antisera, anti-receptor 2394 and anti-receptor 2169, is prepared in M199 medium (Gibco). 200 µl of each dilution are placed in the wells of a microtitration plate (8×12 in.). A control test is carried out with 200 µl of M199 medium. Into each of the wells there are added (i) 100 µl of a culture in the exponential growth phase of a strain of *N. meningitidis*, in Mueller-Hinton medium supplemented with 30 µM EDDA and (ii) 100 µl of complement (young rabbit serum, diluted).

After 30 min of incubation at 37° C. with gentle agitation, 1 ml of Mueller-Hinton medium containing 1 ml of Noble agar in the supercooled state is added into each well. After solidification of the medium, incubation is carried out for 18–24 hours at 37° C.; the number of colony forming units in each well is then evaluated. The reciprocal of the final dilution of antiserum in the presence of which a 50% lysis is observed relative to the control corresponds to the bactericidal titre.

The results are presented in Table III below:

| | Bactericidal activity | | | |
|---|---|---|---|---|
| | Rabbit No. 1 | | Rabbit No. 2 | |
| | Serum before 2394 immunisation | Anti-receptor antiserum | Serum before 2169 immunisation | Anti-receptor antiserum |
| 2394 | <8 | 2048 | <8 | <8 |
| 2228 | <8 | 1024 | <8 | <8 |
| 2154 | <8 | 2048 | <8 | <8 |
| 2234 | <8 | 2048 | <8 | <8 |
| 2448 | <8 | 256 | <8 | <4 |
| 2169 | <16 | <16 | <8 | 1024 |
| 896 | <8 | <8 | <8 | 65 |

The anti-receptor 2394 antiserum has bactericidal activity exclusively against strains of the first type as defined in the present application (2394, 2228, 2154, 2234 and 2448), while the anti-receptor 2169 antiserum has bactericidal activity exclusively against strains of the second type (2169 and 876). This strongly suggests that the production of neutralising antibodies is essentially induced by the lower molecular weight subunit which carries the antigenic variability.

I claim:

1. A vaccinal pharmaceutical composition intended for preventing a *Neisseria meningitidis* infection, which comprises, as therapeutic agents, at least a first and a second molecule capable of binding to human transferrin which are either a human transferrin receptor of *N. meningitidis* or a subunit thereof; the said first molecule originating from a first strain of *N. meningitidis* which possesses a human transferrin receptor comprising a high molecular weight subunit and a lower molecular weight subunit, and in which the lower molecular weight subunit is recognised by an antiserum to the receptor of *N. meningitidis* strain 2394 (receptor 2394) and is not recognised by an antiserum to the receptor of *N. meningitidis* strain 2169 (receptor 2169); and the said second molecule originating from a second strain of *N. meningitidis* which possesses a human transferrin receptor comprising a high molecular weight subunit and a lower molecular weight subunit, and in which the lower molecular weight subunit is recognised by an anti-receptor 2169 antiserum and is not recognised by an anti-receptor 2394 antiserum.

2. A vaccinal pharmaceutical composition according to claim 1, which comprises, as therapeutic agents, at least a first and a second molecule capable of binding human transferrin; the said first molecule originating from a first strain of *N. meningitidis* which possesses a human transferrin receptor in which the high molecular subunit weight and the lower molecular weight subunit are recognised by an anti-receptor 2394 antiserum; and the said second molecule originating from a second strain of *N. meningitidis* which possesses a human transferrin receptor in which the high molecular weight subunit and the lower molecular weight subunit are recognised by an anti-receptor 2169 antiserum.

3. A vaccinal pharmaceutical composition according to claims 1 or 2, which comprises, as therapeutic agents, at least a first and a second molecule capable of binding to human transferrin; the said first molecule originating from a first strain of *N. meningitidis* which possesses a human transferrin receptor comprising a subunit of high molecular weight of 100 kD approximately to 90 kD and a subunit of lower molecular weight of 75 kD to 60 kD; and the said second molecule originating from a second strain of *N. meningitidis* which possesses a human transferrin receptor comprising of a subunit of high molecular weight of 100 kD approximately to 90 kD and a subunit of lower molecular weight of 90 kD to 80 kD.

4. A vaccinal pharmaceutical composition according to claim 3, in which the said first molecule originates from a first strain of *N. meningitidis* which possesses a human transferrin receptor comprising a subunit of high molecular weight of 93–95 kD approximately and a subunit of lower molecular weight of 72 kD to 65 kD.

5. A vaccinal pharmaceutical composition according to claim 4, in which the said first molecule originates from a first strain of *N. meningitidis* which possesses a human transferrin receptor comprising a subunit of high molecular weight of 93 kD approximately and a subunit of lower molecular weight of 67–70 kD approximately.

6. A vaccinal pharmaceutical composition according to claim 5, in which the said second molecule originates from a second strain of *N. meningitidis* which possesses a human transferrin receptor comprising a subunit of high molecular weight of 100 kD approximately to 95 kD and a subunit of lower molecular weight of 87 kD to 85 kD.

7. A vaccinal pharmaceutical composition according to claim 6, in which the said second molecule originates from a second strain of *N. meningitidis* which possesses a human transferrin receptor comprising a subunit of high molecular weight of 98 kD approximately and a subunit of lower molecular weight of 87 kD approximately.

8. A vaccinal pharmaceutical composition according to claim 1, in which the said first and second molecules originate respectively from a first and second strain of *N. meningitidis* serogroup B.

9. A vaccinal pharmaceutical composition for preventing a *Neisseria meningitidis* infection, which comprises therapeutic agents comprising a first and a second molecule capable of binding to human transferrin which are either a human transferrin receptor of *N. meningitidis* or a subunit thereof; said first molecule originating from a first strain of *N. meningitidis* which possesses a human transferrin receptor comprising a high molecular weight subunit and a lower molecular weight subunit, and in which the lower molecular weight subunit is recognized by an antiserum to the receptor of *N. meningitidis* strain 2394 and is not recognized by an antiserum to the receptor of *N. meningitidis* strain 2169, and said second molecule, originating from a second strain of *N. meningitidis* which possesses a human transferrin receptor comprising a high molecular weight subunit and a lower molecular weight subunit, and in which the lower molecular weight subunit is recognized by an antiserum to the receptor of *N. meningitidis* strain 2169 and is not recognized by an antiserum to the receptor of *N. meningitidis* strain 2394.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 579 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Neisseria meningitidis 2394 subunit Tbp2.

( x i ) SEQUENCE DESCRIPTION: SEQ ID NO:1:

| Cys | Leu | Gly | Gly | Gly | Gly | Ser | Phe | Asp | Leu | Asp | Ser | Val | Glu | Thr | Val |
|---|---|---|---|---|---|---|---|---|---|---|---|---|---|---|---|
| 1 | | | | 5 | | | | | 10 | | | | | 15 | |

```
Gln Asp Met His Ser Lys Pro Lys Tyr Glu Asp Glu Lys Ser Gln Pro
         20                      25                      30
    Glu Ser Gln Gln Asp Val Ser Glu Asn Ser Gly Ala Ala Tyr Gly Phe
             35                      40                      45
Ala Val Lys Leu Pro Arg Arg Asn Ala His Phe Asn Pro Lys Tyr Lys
 50                      55                      60
Glu Lys His Lys Pro Leu Gly Ser Met Asp Trp Lys Lys Leu Gln Arg
 65                      70                      75                  80
Gly Glu Pro Asn Ser Phe Ser Glu Arg Asp Glu Leu Glu Lys Lys Arg
                 85                      90                      95
Gly Ser Ser Glu Leu Ile Glu Ser Lys Trp Glu Asp Gly Gln Ser Arg
             100                     105                     110
Val Val Gly Tyr Thr Asn Phe Thr Tyr Val Arg Ser Gly Tyr Val Tyr
         115                     120                     125
Leu Asn Lys Asn Asn Ile Asp Ile Lys Asn Asn Ile Val Leu Phe Gly
     130                     135                     140
Pro Asp Gly Tyr Leu Tyr Tyr Lys Gly Lys Glu Pro Ser Lys Glu Leu
145                     150                     155                     160
Pro Ser Glu Lys Ile Thr Tyr Lys Gly Thr Trp Asp Tyr Val Thr Asp
                 165                     170                     175
Ala Met Glu Lys Gln Arg Phe Glu Gly Leu Gly Ser Ala Ala Gly Gly
             180                     185                     190
Asp Lys Ser Gly Ala Leu Ser Ala Leu Glu Glu Gly Val Leu Arg Asn
         195                     200                     205
Gln Ala Glu Ala Ser Ser Gly His Thr Asp Phe Gly Met Thr Ser Glu
     210                     215                     220
Phe Glu Val Asp Phe Ser Asp Lys Thr Ile Lys Gly Thr Leu Tyr Arg
225                     230                     235                     240
Asn Asn Arg Ile Thr Gln Asn Asn Ser Glu Asn Lys Gln Ile Lys Thr
                 245                     250                     255
Thr Arg Tyr Thr Ile Gln Ala Thr Leu His Gly Asn Arg Phe Lys Gly
             260                     265                     270
Lys Ala Leu Ala Ala Asp Lys Gly Ala Thr Asn Gly Ser His Pro Phe
         275                     280                     285
Ile Ser Asp Ser Asp Ser Leu Glu Gly Gly Phe Tyr Gly Pro Lys Gly
     290                     295                     300
Glu Glu Leu Ala Gly Lys Phe Leu Ser Asn Asp Asn Lys Val Ala Ala
305                     310                     315                     320
Val Phe Gly Ala Lys Gln Lys Asp Lys Lys Asp Gly Glu Asn Ala Ala
                 325                     330                     335
Gly Pro Ala Thr Glu Thr Val Ile Asp Ala Tyr Arg Ile Thr Gly Glu
             340                     345                     350
Glu Phe Lys Lys Glu Gln Ile Asp Ser Phe Gly Asp Val Lys Lys Leu
         355                     360                     365
Leu Val Asp Gly Val Glu Leu Ser Leu Leu Pro Ser Glu Gly Asn Lys
     370                     375                     380
 Ala Ala Phe Gln His Glu Ile Glu Gln Asn Gly Val Lys Ala Thr Val
385                     390                     395                     400
Cys Cys Ser Asn Leu Asp Tyr Met Ser Phe Gly Lys Leu Ser Lys Glu
                 405                     410                     415
Asn Lys Asp Asp Met Phe Leu Gln Gly Val Arg Thr Pro Val Ser Asp
             420                     425                     430
Val Ala Ala Arg Thr Glu Ala Lys Tyr Arg Gly Thr Gly Thr Trp Tyr
         435                     440                     445
```

| | | | | | | | | | | | | | | |
|---|---|---|---|---|---|---|---|---|---|---|---|---|---|---|
| Gly | Tyr 450 | Ile | Ala | Asn | Gly | Thr 455 | Ser | Trp | Ser | Gly | Glu 460 | Ala | Ser | Asn | Gln |
| Glu 465 | Gly | Gly | Asn | Arg | Ala 470 | Glu | Phe | Asp | Val | Asp 475 | Phe | Ser | Thr | Lys | Lys 480 |
| Ile | Ser | Gly | Thr | Leu 485 | Thr | Ala | Lys | Asp | Arg 490 | Thr | Ser | Pro | Ala | Phe 495 | Thr |
| Ile | Thr | Ala | Met 500 | Ile | Lys | Asp | Asn | Gly 505 | Phe | Ser | Gly | Val | Ala 510 | Lys | Thr |
| Gly | Glu | Asn 515 | Gly | Phe | Ala | Leu | Asp 520 | Pro | Gln | Asn | Thr | Gly 525 | Asn | Ser | His |
| Tyr | Thr 530 | His | Ile | Glu | Ala | Thr 535 | Val | Ser | Gly | Gly | Phe 540 | Tyr | Gly | Lys | Asn |
| Ala 545 | Ile | Glu | Met | Gly | Gly 550 | Ser | Phe | Ser | Phe | Pro 555 | Gly | Asn | Ala | Pro | Glu 560 |
| Gly | Lys | Gln | Glu | Lys 565 | Ala | Ser | Val | Val | Phe 570 | Gly | Ala | Lys | Arg | Gln 575 | Gln |
| Leu | Val | Gln | | | | | | | | | | | | | |

( 2 ) INFORMATION FOR SEQ ID NO:2:

( i ) SEQUENCE CHARACTERISTICS:
( A ) LENGTH: 884 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Neisseria meningitidis 2394 subunit Tbp1.

( x i ) SEQUENCE DESCRIPTION: SEQ ID NO:2:

| | | | | | | | | | | | | | | |
|---|---|---|---|---|---|---|---|---|---|---|---|---|---|---|
| Glu 1 | Asn | Val | Gln | Ala 5 | Glu | Gln | Ala | Gln | Glu 10 | Lys | Gln | Leu | Asp | Thr 15 | Ile |
| Gln | Val | Lys | Ala 20 | Lys | Lys | Gln | Lys | Thr 25 | Arg | Arg | Asp | Asn | Glu 30 | Val | Thr |
| Gly | Leu | Gly 35 | Lys | Leu | Val | Lys | Ser 40 | Ser | Asp | Thr | Leu | Ser 45 | Lys | Glu | Gln |
| Val | Leu 50 | Asn | Ile | Arg | Asp | Leu 55 | Thr | Arg | Tyr | Asp | Pro 60 | Gly | Ile | Ala | Val |
| Val 65 | Glu | Gln | Gly | Arg | Gly 70 | Ala | Ser | Ser | Gly | Tyr 75 | Ser | Ile | Arg | Gly | Met 80 |
| Asp | Lys | Asn | Arg | Val 85 | Ser | Leu | Thr | Val | Asp 90 | Gly | Val | Ser | Gln | Ile 95 | Gln |
| Ser | Tyr | Thr | Ala 100 | Gln | Ala | Ala | Leu | Gly 105 | Gly | Thr | Arg | Thr | Ala 110 | Gly | Ser |
| Ser | Gly | Ala 115 | Ile | Asn | Glu | Ile | Glu 120 | Tyr | Glu | Asn | Val | Lys 125 | Ala | Val | Glu |
| Ile | Ser | Lys 130 | Gly | Ser | Asn | Ser 135 | Ser | Glu | Tyr | Gly | Asn 140 | Gly | Ala | Leu | Ala |
| Gly 145 | Ser | Val | Ala | Phe | Gln 150 | Thr | Lys | Thr | Ala | Ala 155 | Asp | Ile | Ile | Gly | Glu 160 |
| Gly | Lys | Gln | Trp | Gly 165 | Ile | Gln | Ser | Lys | Thr 170 | Ala | Tyr | Ser | Gly | Lys 175 | Asp |
| His | Ala | Leu | Thr 180 | Gln | Ser | Leu | Ala | Leu 185 | Ala | Gly | Arg | Ser | Gly 190 | Gly | Ala |
| Glu | Ala | Leu | Leu | Ile | Tyr | Thr | Lys | Arg | Arg | Gly | Arg | Glu | Ile | His | Ala |

```
                         195                          200                          205
    His  Lys  Asp  Ala  Gly  Lys  Gly  Val  Gln  Ser  Phe  Asn  Arg  Leu  Val  Leu
         210                      215                      220

Asp  Glu  Asp  Lys  Lys  Glu  Gly  Gly  Ser  Gln  Tyr  Arg  Tyr  Phe  Ile  Val
    225                      230                      235                          240

Glu  Glu  Glu  Cys  His  Asn  Gly  Tyr  Ala  Ala  Cys  Lys  Asn  Lys  Leu  Lys
                   245                      250                          255

Glu  Asp  Ala  Ser  Val  Lys  Asp  Glu  Arg  Lys  Thr  Val  Ser  Thr  Gln  Asp
                        260                      265                      270

Tyr  Thr  Gly  Ser  Asn  Arg  Leu  Leu  Ala  Asn  Pro  Leu  Glu  Tyr  Gly  Ser
                   275                      280                      285

Gln  Ser  Trp  Leu  Phe  Arg  Pro  Gly  Trp  His  Leu  Asp  Asn  Arg  His  Tyr
         290                      295                      300

Val  Gly  Ala  Val  Leu  Glu  Arg  Thr  Gln  Gln  Thr  Phe  Asp  Thr  Arg  Asp
    305                      310                      315                          320

Met  Thr  Val  Pro  Ala  Tyr  Phe  Thr  Ser  Glu  Asp  Tyr  Val  Pro  Gly  Ser
                        325                      330                      335

Leu  Lys  Gly  Leu  Gly  Lys  Tyr  Ser  Gly  Asp  Asn  Lys  Ala  Glu  Arg  Leu
                        340                      345                      350

Phe  Val  Gln  Gly  Glu  Gly  Ser  Thr  Leu  Gln  Gly  Ile  Gly  Tyr  Gly  Thr
                   355                      360                      365

Gly  Val  Phe  Tyr  Asp  Glu  Arg  His  Thr  Lys  Asn  Arg  Tyr  Gly  Val  Glu
    370                      375                      380

Tyr  Val  Tyr  His  Asn  Ala  Asp  Lys  Asp  Thr  Trp  Ala  Asp  Tyr  Ala  Arg
    385                      390                      395                          400

Leu  Ser  Tyr  Asp  Arg  Gln  Gly  Ile  Asp  Leu  Asp  Asn  Arg  Leu  Gln  Gln
                             405                      410                      415

Thr  His  Cys  Ser  His  Asp  Gly  Ser  Asp  Lys  Asn  Cys  Arg  Pro  Asp  Gly
                             420                      425                      430

Asn  Lys  Pro  Tyr  Ser  Phe  Tyr  Lys  Ser  Asp  Arg  Met  Ile  Tyr  Glu  Glu
                   435                      440                      445

Ser  Arg  Asn  Leu  Phe  Gln  Ala  Val  Phe  Lys  Lys  Ala  Phe  Asp  Thr  Ala
         450                      455                      460

Lys  Ile  Arg  His  Asn  Leu  Ser  Ile  Asn  Leu  Gly  Tyr  Asp  Arg  Phe  Lys
    465                      470                      475                          480

Ser  Gln  Leu  Ser  His  Ser  Asp  Tyr  Tyr  Leu  Gln  Asn  Ala  Val  Gln  Ala
                        485                      490                      495

Tyr  Asp  Leu  Ile  Thr  Pro  Lys  Lys  Pro  Pro  Phe  Pro  Asn  Gly  Ser  Lys
                        500                      505                      510

Asp  Asn  Pro  Tyr  Arg  Val  Ser  Ile  Gly  Lys  Thr  Thr  Val  Asn  Thr  Ser
                   515                      520                      525

Pro  Ile  Cys  Arg  Phe  Gly  Asn  Asn  Thr  Tyr  Thr  Asp  Cys  Thr  Pro  Arg
         530                      535                      540

Asn  Ile  Gly  Gly  Asn  Gly  Tyr  Tyr  Ala  Ala  Val  Gln  Asp  Asn  Val  Arg
    545                      550                      555                          560

Leu  Gly  Arg  Trp  Ala  Asp  Val  Gly  Ala  Gly  Ile  Arg  Tyr  Asp  Tyr  Arg
                        565                      570                      575

Ser  Thr  His  Ser  Glu  Asp  Lys  Ser  Val  Ser  Thr  Gly  Thr  His  Arg  Asn
                   580                      585                      590

Leu  Ser  Trp  Asn  Ala  Gly  Val  Val  Leu  Lys  Pro  Phe  Thr  Trp  Met  Asp
         595                      600                      605

Leu  Thr  Tyr  Arg  Ala  Ser  Thr  Gly  Phe  Arg  Leu  Pro  Ser  Phe  Ala  Glu
    610                      615                      620
```

| Met | Tyr | Gly | Trp | Arg | Ala | Gly | Glu | Ser | Leu | Lys | Thr | Leu | Asp | Leu | Lys |
| 625 | | | | | 630 | | | | | 635 | | | | | 640 |
| Pro | Glu | Lys | Ser | Phe | Asn | Arg | Glu | Ala | Gly | Ile | Val | Phe | Lys | Gly | Asp |
| | | | | 645 | | | | | 650 | | | | | 655 | |
| Phe | Gly | Asn | Leu | Glu | Ala | Ser | Tyr | Phe | Asn | Asn | Ala | Tyr | Arg | Asp | Leu |
| | | | 660 | | | | | 665 | | | | | 670 | | |
| Ile | Ala | Phe | Gly | Tyr | Glu | Thr | Arg | Thr | Gln | Asn | Gly | Gln | Thr | Ser | Ala |
| | | 675 | | | | | 680 | | | | | 685 | | | |
| Ser | Gly | Asp | Pro | Gly | Tyr | Arg | Asn | Ala | Gln | Asn | Ala | Arg | Ile | Ala | Gly |
| | 690 | | | | | 695 | | | | | 700 | | | | |
| Ile | Asn | Ile | Leu | Gly | Lys | Ile | Asp | Trp | His | Gly | Val | Trp | Gly | Gly | Leu |
| 705 | | | | | 710 | | | | | 715 | | | | | 720 |
| Pro | Asp | Gly | Leu | Tyr | Ser | Thr | Leu | Ala | Tyr | Asn | Arg | Ile | Lys | Val | Lys |
| | | | | 725 | | | | | 730 | | | | | 735 | |
| Asp | Ala | Asp | Ile | Arg | Ala | Asp | Arg | Thr | Phe | Val | Thr | Ser | Tyr | Leu | Phe |
| | | | 740 | | | | | 745 | | | | | 750 | | |
| Asp | Ala | Val | Gln | Pro | Ser | Arg | Tyr | Val | Leu | Gly | Leu | Gly | Tyr | Asp | His |
| | | 755 | | | | | 760 | | | | | 765 | | | |
| | Pro | Asp | Gly | Ile | Trp | Gly | Ile | Asn | Thr | Met | Phe | Thr | Tyr | Ser | Lys | Ala |
| | 770 | | | | | 775 | | | | | 780 | | | | | |
| Lys | Ser | Val | Asp | Glu | Leu | Leu | Gly | Ser | Gln | Ala | Leu | Leu | Asn | Gly | Asn |
| 785 | | | | | 790 | | | | | 795 | | | | | 800 |
| Ala | Asn | Ala | Lys | Lys | Ala | Ala | Ser | Arg | Arg | Thr | Arg | Pro | Trp | Tyr | Val |
| | | | | 805 | | | | | 810 | | | | | 815 | |
| Thr | Asp | Val | Ser | Gly | Tyr | Tyr | Asn | Ile | Lys | Lys | His | Leu | Thr | Leu | Arg |
| | | | 820 | | | | | 825 | | | | | 830 | | |
| Ala | Gly | Val | Tyr | Asn | Leu | Leu | Asn | Tyr | Arg | Tyr | Val | Thr | Trp | Glu | Asn |
| | | 835 | | | | | 840 | | | | | 845 | | | |
| Val | Arg | Gln | Thr | Ala | Gly | Gly | Ala | Val | Asn | Gln | His | Lys | Asn | Val | Gly |
| | 850 | | | | | 855 | | | | | 860 | | | | |
| Val | Tyr | Asn | Arg | Tyr | Ala | Ala | Pro | Gly | Arg | Asn | Tyr | Thr | Phe | Ser | Leu |
| 865 | | | | | 870 | | | | | 875 | | | | | 880 |
| Glu | Met | Lys | Phe | | | | | | | | | | | | |

( 2 ) INFORMATION FOR SEQ ID NO:3:

( i ) SEQUENCE CHARACTERISTICS:
      ( A ) LENGTH: 887 amino acids
      ( B ) TYPE: amino acid
      ( C ) STRANDEDNESS: single
      ( D ) TOPOLOGY: linear ( i i ) MOLECULE TYPE: protein ( v i ) ORIGINAL SOURCE:
      ( A ) ORGANISM: Neisseria meningitidis 2169 subunit Tbp1.

( x i ) SEQUENCE DESCRIPTION: SEQ ID NO:3:

| Glu | Asn | Val | Gln | Ala | Gly | Gln | Ala | Gln | Glu | Lys | Gln | Leu | Asp | Thr | Ile |
| 1 | | | | 5 | | | | | 10 | | | | | 15 | |
| Gln | Val | Lys | Ala | Lys | Lys | Gln | Lys | Thr | Arg | Arg | Asp | Asn | Glu | Val | Thr |
| | | | 20 | | | | | 25 | | | | | 30 | | |
| Gly | Leu | Gly | Lys | Leu | Val | Lys | Thr | Ala | Asp | Thr | Leu | Ser | Lys | Glu | Gln |
| | | 35 | | | | | 40 | | | | | 45 | | | |
| Val | Leu | Asp | Ile | Arg | Asp | Leu | Thr | Arg | Tyr | Asp | Pro | Gly | Ile | Ala | Val |
| | 50 | | | | | 55 | | | | | 60 | | | | |
| Val | Glu | Gln | Gly | Arg | Gly | Ala | Ser | Ser | Gly | Tyr | Ser | Ile | Arg | Gly | Met |
| 65 | | | | | 70 | | | | | 75 | | | | | 80 |

```
Asp Lys Asn Arg Val Ser Leu Thr Val Asp Gly Leu Ala Gln Ile Gln
                85                  90                  95

Ser Tyr Thr Ala Gln Ala Ala Leu Gly Gly Thr Arg Thr Ala Gly Ser
            100                 105                 110

Ser Gly Ala Ile Asn Glu Ile Glu Tyr Glu Asn Val Lys Ala Val Glu
            115                 120                 125

Ile Ser Lys Gly Ser Asn Ser Val Glu Gln Gly Ser Gly Ala Leu Ala
            130                 135                 140

Gly Ser Val Ala Phe Gln Tyr Lys Thr Ala Asp Asp Val Ile Gly Glu
    145                 150                 155                 160

Gly Arg Gln Trp Gly Ile Gln Ser Lys Thr Ala Tyr Ser Gly Lys Asn
            165                 170                 175

Arg Gly Leu Thr Gln Ser Ile Ala Leu Ala Gly Arg Ile Gly Gly Ala
            180                 185                 190

Glu Ala Leu Leu Ile His Thr Gly Arg Arg Ala Gly Glu Ile Arg Ala
            195                 200                 205

His Glu Asp Ala Gly Arg Gly Val Gln Ser Phe Asn Arg Leu Val Pro
    210                 215                 220

Val Glu Asp Ser Ser Glu Tyr Ala Tyr Phe Ile Val Glu Asp Glu Cys
225                 230                 235                 240

Glu Gly Lys Asn Tyr Glu Thr Cys Lys Ser Lys Pro Lys Lys Asp Val
            245                 250                 255

Val Gly Lys Asp Glu Arg Gln Thr Val Ser Thr Arg Asp Tyr Thr Gly
            260                 265                 270

Pro Asn Arg Phe Leu Ala Asp Pro Leu Ser Tyr Glu Ser Arg Ser Trp
            275                 280                 285

Leu Phe Arg Pro Gly Phe Arg Phe Glu Asn Lys Arg His Tyr Ile Gly
290                 295                 300

Gly Ile Leu Glu His Thr Gln Gln Thr Phe Asp Thr Arg Asp Met Thr
305                 310                 315                 320

Val Pro Ala Phe Leu Thr Lys Ala Val Phe Asp Ala Asn Ser Lys Gln
            325                 330                 335

Ala Gly Ser Leu Pro Gly Asn Gly Lys Tyr Ala Gly Asn His Lys Tyr
            340                 345                 350

Gly Gly Leu Phe Thr Asn Gly Glu Asn Gly Ala Leu Val Gly Ala Glu
            355                 360                 365

Tyr Gly Thr Gly Val Phe Tyr Asp Glu Thr His Thr Lys Ser Arg Tyr
    370                 375                 380

Gly Leu Glu Tyr Val Tyr Thr Asn Ala Asp Lys Asp Thr Trp Ala Asp
385                 390                 395                 400

Tyr Ala Arg Leu Ser Tyr Asp Arg Gln Gly Ile Gly Leu Asp Asn His
            405                 410                 415

Phe Gln Gln Thr His Cys Ser Ala Asp Gly Ser Asp Lys Tyr Cys Arg
            420                 425                 430

Pro Ser Ala Asp Lys Pro Phe Ser Tyr Tyr Lys Ser Asp Arg Val Ile
            435                 440                 445

Tyr Gly Glu Ser His Arg Leu Leu Gln Ala Ala Phe Lys Lys Ser Phe
    450                 455                 460

Asp Thr Ala Lys Ile Arg His Asn Leu Ser Val Asn Leu Gly Phe Asp
465                 470                 475                 480

Arg Phe Asp Ser Asn Leu Arg His Gln Asp Tyr Tyr Gln His Ala
            485                 490                 495

Asn Arg Ala Tyr Ser Ser Lys Thr Pro Pro Lys Thr Ala Asn Pro Asn
```

|             |     |     |     |     |     | 500 |     |     |     |     | 505 |     |     |     |     | 510 |     |     |
|---|---|---|---|---|---|---|---|---|---|---|---|---|---|---|---|---|---|---|

```
                                      500                     505                     510
        Gly    Asp    Lys    Ser    Lys    Pro    Tyr    Trp    Val    Ser    Ile    Gly    Gly    Asn    Val
                      515                           520                          525
        Val    Thr    Gly    Gln    Ile    Cys    Leu    Phe    Gly    Asn    Asn    Thr    Tyr    Thr    Asp    Cys
               530                           535                          540
        Thr    Pro    Arg    Ser    Ile    Asn    Gly    Lys    Ser    Tyr    Tyr    Ala    Ala    Val    Arg    Asp
        545                          550                          555                                        560
        Asn    Val    Arg    Leu    Gly    Arg    Trp    Ala    Asp    Val    Gly    Ala    Gly    Leu    Arg    Tyr
                             565                          570                                 575
        Asp    Tyr    Arg    Ser    Thr    His    Ser    Asp    Asp    Gly    Ser    Val    Ser    Thr    Gly    Thr
                             580                          585                          590
        His    Arg    Thr    Leu    Ser    Trp    Asn    Ala    Gly    Ile    Val    Leu    Lys    Pro    Ala    Asp
                      595                          600                          605
        Trp    Leu    Asp    Leu    Thr    Tyr    Arg    Thr    Ser    Thr    Gly    Phe    Arg    Leu    Pro    Ser
               610                          615                          620
        Phe    Ala    Glu    Met    Tyr    Gly    Trp    Arg    Ser    Gly    Val    Gln    Ser    Lys    Ala    Val
        625                                 630                          635                                 640
        Lys    Ile    Asp    Pro    Glu    Lys    Ser    Phe    Asn    Lys    Glu    Ala    Gly    Ile    Val    Phe
                             645                          650                                 655
        Lys    Gly    Asp    Phe    Gly    Asn    Leu    Glu    Ala    Ser    Trp    Phe    Asn    Asn    Ala    Tyr
                      660                          665                          670
        Arg    Asp    Leu    Ile    Val    Arg    Gly    Tyr    Glu    Ala    Gln    Ile    Lys    Asn    Gly    Lys
                      675                          680                          685
        Glu    Glu    Ala    Lys    Gly    Asp    Pro    Ala    Tyr    Leu    Asn    Ala    Gln    Ser    Ala    Arg
               690                          695                          700
        Ile    Thr    Gly    Ile    Asn    Ile    Leu    Gly    Lys    Ile    Asp    Trp    Asn    Gly    Val    Trp
        705                          710                          715                                        720
        Asp    Lys    Leu    Pro    Glu    Gly    Trp    Tyr    Ser    Thr    Phe    Ala    Tyr    Asn    Arg    Val
                             725                          730                                 735
        His    Val    Arg    Asp    Ile    Lys    Lys    Arg    Ala    Asp    Arg    Thr    Asp    Ile    Gln    Ser
                      740                          745                          750
        His    Leu    Phe    Asp    Ala    Ile    Gln    Pro    Ser    Arg    Tyr    Val    Val    Gly    Leu    Gly
                      755                          760                          765
        Tyr    Asp    Gln    Pro    Glu    Gly    Lys    Trp    Gly    Val    Asn    Gly    Met    Leu    Thr    Tyr
        770                          775                          780
        Ser    Lys    Ala    Lys    Glu    Ile    Thr    Glu    Leu    Leu    Gly    Ser    Arg    Ala    Leu    Leu
        785                          790                          795                                        800
        Asn    Gly    Asn    Ser    Arg    Asn    Thr    Lys    Ala    Thr    Ala    Arg    Arg    Thr    Arg    Pro
                             805                          810                                 815
        Trp    Tyr    Ile    Val    Asp    Val    Ser    Gly    Tyr    Tyr    Thr    Ile    Lys    Lys    His    Phe
                             820                          825                          830
        Thr    Leu    Arg    Ala    Gly    Val    Tyr    Asn    Leu    Leu    Asn    Tyr    Arg    Tyr    Val    Thr
                      835                          840                          845
          Trp    Glu    Asn    Val    Arg    Gln    Thr    Ala    Gly    Gly    Ala    Val    Asn    Gln    His    Lys
                 850                          855                          860
          Asn    Val    Gly    Val    Tyr    Asn    Arg    Tyr    Ala    Ala    Pro    Gly    Arg    Asn    Tyr    Thr
          865                          870                          875                                        880
          Phe    Ser    Leu    Glu    Met    Lys    Phe
                               885
```

( 2 ) INFORMATION FOR SEQ ID NO:4:

( i ) SEQUENCE CHARACTERISTICS:
( A ) LENGTH: 691 amino acids
( B ) TYPE: amino acid (C) STRANDEDNESS: single
(D) TOPOLOGY: linear (ii) MOLECULE TYPE: protein (vi) ORIGINAL SOURCE:
 (A) ORGANISM: Neisseria meningitidis 2169 subunit Tbp2.

(xi) SEQUENCE DESCRIPTION: SEQ ID NO:4:

```
Cys Leu Gly Gly Gly Gly Ser Phe Asp Leu Asp Ser Val Asp Thr Glu
1               5                   10                  15

Ala Pro Arg Pro Ala Pro Lys Tyr Gln Asp Val Ser Ser Glu Lys Pro
            20                  25                  30

Gln Ala Gln Lys Asp Gln Gly Gly Tyr Gly Phe Ala Met Arg Leu Lys
        35                  40                  45

Arg Arg Asn Trp Tyr Pro Gly Ala Glu Glu Ser Glu Val Lys Leu Asn
    50                  55                  60

Glu Ser Asp Trp Glu Ala Thr Gly Leu Pro Thr Lys Pro Lys Glu Leu
65                  70                  75                  80

Pro Lys Arg Gln Lys Ser Val Ile Glu Lys Val Glu Thr Asp Gly Asp
                85                  90                  95

Ser Asp Ile Tyr Ser Ser Pro Tyr Leu Thr Pro Ser Asn His Gln Asn
            100                 105                 110

Gly Ser Ala Gly Asn Gly Val Asn Gln Pro Lys Asn Gln Ala Thr Gly
        115                 120                 125

His Glu Asn Phe Gln Tyr Val Tyr Ser Gly Trp Phe Tyr Lys His Ala
    130                 135                 140

Ala Ser Glu Lys Asp Phe Ser Asn Lys Lys Ile Lys Ser Gly Asp Asp
145                 150                 155                 160

Gly Tyr Ile Phe Tyr His Gly Glu Lys Pro Ser Arg Gln Leu Pro Ala
                165                 170                 175

Ser Gly Lys Val Ile Tyr Lys Gly Val Trp His Phe Val Thr Asp Thr
            180                 185                 190

Lys Lys Gly Gln Asp Phe Arg Glu Ile Ile Gln Pro Ser Lys Lys Gln
        195                 200                 205

Gly Asp Arg Tyr Ser Gly Phe Ser Gly Asp Gly Ser Glu Glu Tyr Ser
    210                 215                 220

Asn Lys Asn Glu Ser Thr Leu Lys Asp Asp His Glu Gly Tyr Gly Phe
225                 230                 235                 240

Thr Ser Asn Leu Glu Val Asp Phe Gly Asn Lys Lys Leu Thr Gly Lys
                245                 250                 255

Leu Ile Arg Asn Asn Ala Ser Leu Asn Asn Thr Asn Asn Asp Lys
            260                 265                 270

His Thr Thr Gln Tyr Tyr Ser Leu Asp Ala Gln Ile Thr Gly Asn Arg
        275                 280                 285

Phe Asn Gly Thr Ala Thr Ala Thr Asp Lys Lys Glu Asn Glu Thr Lys
    290                 295                 300

Leu His Pro Phe Val Ser Asp Ser Ser Leu Ser Gly Gly Phe Phe
305                 310                 315                 320

Gly Pro Gln Gly Glu Glu Leu Gly Phe Arg Phe Leu Ser Asp Asp Gln
                325                 330                 335

Lys Val Ala Val Val Gly Ser Ala Lys Thr Lys Asp Lys Leu Glu Asn
            340                 345                 350

Gly Ala Ala Ala Ser Gly Ser Thr Gly Ala Ala Ala Ser Gly Gly Ala
        355                 360                 365

Ala Gly Thr Ser Ser Glu Asn Ser Lys Leu Thr Thr Val Leu Asp Ala
```

|   |   |   | 370 |   |   |   | 375 |   |   |   | 380 |   |   |   |
|---|---|---|---|---|---|---|---|---|---|---|---|---|---|---|
| Val 385 | Glu | Leu | Thr | Leu | Asn 390 | Asp | Lys | Lys | Ile | Lys 395 | Asn | Leu | Asp | Asn Phe 400 |
| Ser | Asn | Ala | Ala | Gln 405 | Leu | Val | Val | Asp | Gly 410 | Ile | Met | Ile | Pro | Leu Leu 415 |
| Pro | Lys | Asp | Ser 420 | Glu | Ser | Gly | Asn | Thr 425 | Gln | Ala | Asp | Lys | Gly 430 | Lys Asn |
| Gly | Gly | Thr 435 | Glu | Phe | Thr | Arg | Lys 440 | Phe | Glu | His | Thr | Pro 445 | Glu | Ser Asp |
| Lys | Lys 450 | Asp | Ala | Gln | Ala | Gly 455 | Thr | Gln | Thr | Asn | Gly 460 | Ala | Gln | Thr Ala |
| Ser 465 | Asn | Thr | Ala | Gly | Asp 470 | Thr | Asn | Gly | Lys | Thr 475 | Lys | Thr | Tyr | Glu Val 480 |
| Glu | Val | Cys | Cys | Ser 485 | Asn | Leu | Asn | Tyr | Leu 490 | Lys | Tyr | Gly | Met | Leu Thr 495 |
| Arg | Lys | Asn | Ser 500 | Lys | Ser | Ala | Met | Gln 505 | Ala | Gly | Gly | Asn | Ser 510 | Ser Gln |
| Ala | Asp | Ala 515 | Lys | Thr | Glu | Gln | Val 520 | Glu | Gln | Ser | Met | Phe 525 | Leu | Gln Gly |
| Glu | Arg 530 | Thr | Asp | Glu | Lys | Glu 535 | Ile | Pro | Thr | Asp | Gln 540 | Asn | Val | Val Tyr |
| Arg 545 | Gly | Ser | Trp | Tyr | Gly 550 | His | Ile | Ala | Asn | Gly 555 | Thr | Ser | Trp | Ser Gly 560 |
| Asn | Ala | Ser | Asp | Lys 565 | Glu | Gly | Gly | Asn | Arg 570 | Ala | Glu | Phe | Thr | Val Asn 575 |
|   | Phe | Ala | Asp | Lys 580 | Lys | Ile | Thr | Gly | Lys 585 | Leu | Thr | Ala | Glu | Asn Arg Gln 590 |
| Ala | Gln | Thr 595 | Phe | Thr | Ile | Glu | Gly 600 | Met | Ile | Gln | Gly | Asn 605 | Gly | Phe Glu |
| Gly | Thr 610 | Ala | Lys | Thr | Ala | Glu 615 | Ser | Gly | Phe | Asp | Leu 620 | Asp | Gln | Lys Asn |
| Thr 625 | Thr | Arg | Thr | Pro | Lys 630 | Ala | Tyr | Ile | Thr | Asp 635 | Ala | Lys | Val | Lys Gly 640 |
| Gly | Phe | Tyr | Gly | Pro 645 | Lys | Ala | Glu | Glu | Leu 650 | Gly | Gly | Trp | Phe | Ala Tyr 655 |
| Pro | Gly | Asp | Lys 660 | Gln | Thr | Glu | Lys | Ala 665 | Thr | Ala | Thr | Ser | Ser 670 | Asp Gly |
| Asn | Ser | Ala 675 | Ser | Ser | Ala | Thr | Val 680 | Val | Phe | Gly | Ala | Lys 685 | Arg | Gln Gln |
| Pro | Val 690 | Gln |   |   |   |   |   |   |   |   |   |   |   |   |